Sept. 3, 1963 E. S. BOERNER Plant Pat. 2,279
CHRYSANTHEMUM PLANT
Filed Aug. 22, 1962
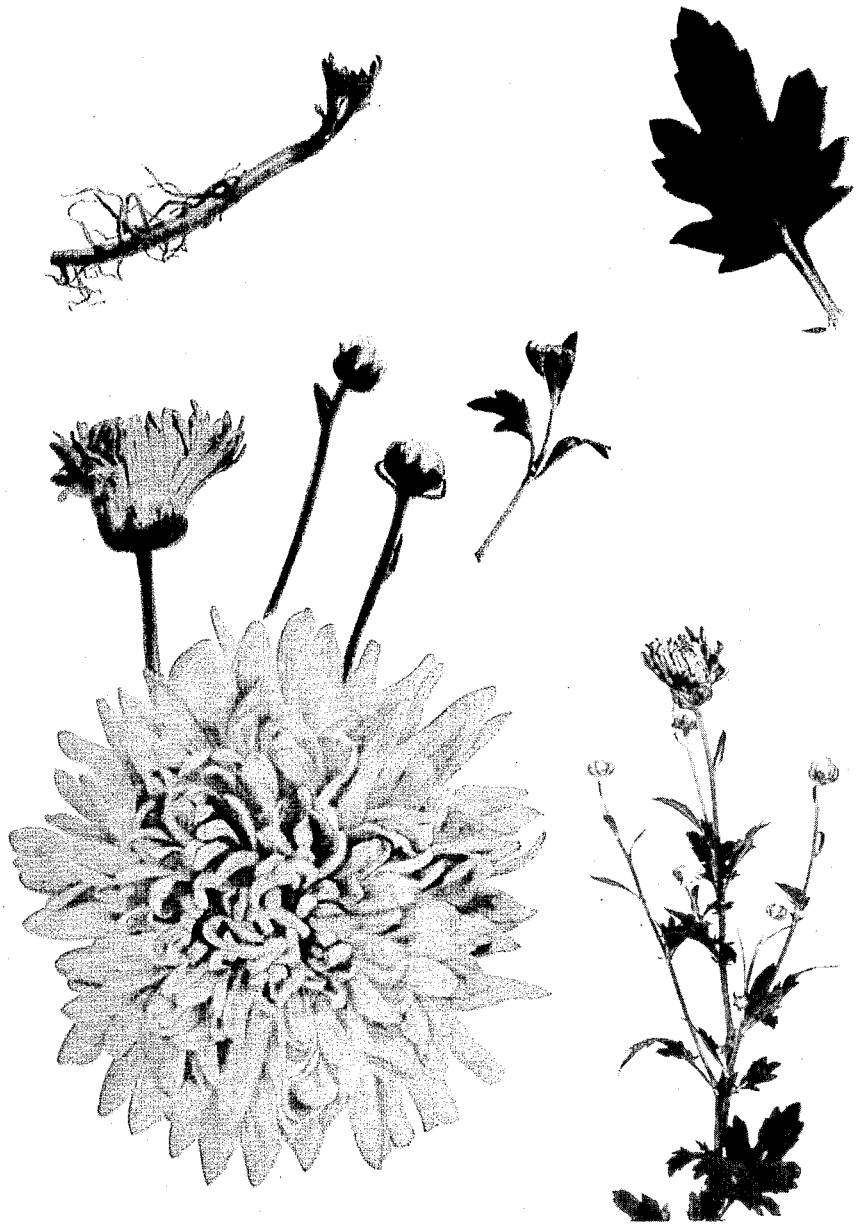
Inventor.
E. S. Boerner
By: Robb & Robb
Attorneys.

United States Patent Office

Plant Pat. 2,279
Patented Sept. 3, 1963

2,279
CHRYSANTHEMUM PLANT

Eugene S. Boerner, Newark, N.Y., assignor to Jackson & Perkins Company, Newark, N.Y., a corporation of New York Filed Aug. 22, 1962, Ser. No. 218,796
1 Claim. (Cl. Plt.—82)

The present invention relates to a new and distinct variety of chrysanthemum plant of the decorative class, which was originated by me by crossing an unnamed and unpatented seedling derived from a cross of "Meadowlark" (Plant Patent No. 1,305) × "Thrush" (Plant Patent No. 1,168) with an unnamed and unpatented large-flowered Hortorum seedling.

The primary objective of this breeding was to produce a new chrysanthemum variety in which there is combined the strength and vigorous habit of plant growth of the unnamed parent seedling derived from "Meadowlark" × "Thrush," and the large flower size and color radiance of the unnamed Hortorum seedling parent. This objective was fully achieved, along with other desirable improvements, as evidenced by the following unique combination of characteristics which are outstanding in the new variety and which distinguish it from its parents, as well as from all other varieties of which I am aware:

(1) A strong and vigorous habit of growth;
(2) A free and airy type of growth;
(3) Leathery foliage texture;
(4) Large size and decorative, double form of the flowers; and
(5) A distinctive and attractive general color tonality of the flowers corresponding to Scarlet, lightly overcast with Scarlet-Red.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations of specimens grown outdoors at Newark, New York, in early morning during the middle part of the month of October:

Parentage: Seedling.
*Seed parent.*—An unnamed seedling of "Meadowlark" × "Thrush."

*Pollen parent.*—An unnamed large-flowered Hortorum seedling.
Classification: Decorative.
Growth: Free; attains height of about 25 inches.
Cold resistance: Hardy in northern New York State.
Blooming period: From middle of September until frost.

*Flower*

Bud:
*Color.*—When sepals first divide—Scarlet, Plate 1, with center of petal lightly overcast with Scarlet-Red, Plate 1. When petals begin to unfurl—Scarlet, Plate 1. When half-blown: inside—Scarlet-Red, Plate 1, lightly overcast with Scarlet, Plate 1; outside—Scarlet, Plate 1, lightly overcast with Carnelian Red, Plate 14.
*Peduncle.*—Color—Yellowish Olive, Plate 30. Strength—strong.

Bloom:
*Size.*—5½ inches.
*Stem.*—Strong.
*Form.*—Decorative.
*Petalage.*—Double.
*Color.*—Center of flower—Scarlet-Red, Plate 1, overcast with Scarlet, Plate 1. Outer petals—Scarlet, Plate 1. Base of petals—Strontian Yellow, Plate 16. Inside of petals—Scarlet, Plate 1, lightly overcast with Scarlet-Red, Plate 1. Reverse of petals—Pale Orange-Yellow, Plate 3, lightly overcast with Scarlet, Plate 1.
*Petals.*—Texture—Medium. Form—Oval.
*Fragrance.*—Characteristic chrysanthemum.

*Plant*

Form: Upright.
Growth: Free; airy; strong; vigorous.
Foliage:
*Size.*—Medium.
*Quantity.*—Normal.
*Color.*—Upper side—Dark Cress Green, Plate 31. Reverse side—Bice Green, Plate 17.
*Texture.*—Leathery.

I claim:

A new and distinct variety of chrysanthemum plant of the decorative class, substantially as herein shown and described, characterized particularly as to novelty by the unique combination of a strong and vigorous habit of growth, a free and airy type of growth, large size and decorative, double form of the flowers, leathery foliage texture, and a distinctive and attractive general color tonality of the flowers corresponding to Scarlet, lightly overcast with Scarlet-Red.

No references cited.